United States Patent [19]

Davis et al.

[11] 4,334,111
[45] Jun. 8, 1982

[54] PROCESS FOR PREPARING SUBSTITUTED BENZOTRIHALIDES

[75] Inventors: Ralph A. Davis; R. Garth Pews, both of Midland, Mich.

[73] Assignee: The Dow Chemical Company, Midland, Mich.

[21] Appl. No.: 878,845

[22] Filed: Feb. 17, 1978

[51] Int. Cl.³ .............................................. C07C 21/24
[52] U.S. Cl. ..................................... 570/143; 570/144; 570/193; 570/195; 568/637; 568/645; 568/649; 568/655; 568/663; 568/933; 568/939; 260/465 G; 564/183; 564/184
[58] Field of Search ........... 260/651 F, 651 R, 465 G; 568/649, 645, 655, 637, 663, 933, 939; 570/143, 144, 193, 195; 564/183, 184, 155, 159

[56] References Cited
U.S. PATENT DOCUMENTS
3,283,018 11/1966 Christe et al. ................... 260/651 F OTHER PUBLICATIONS
Christe & Pavlath, *J. Org. Chem.* 30, 3170 (1965).

Primary Examiner—Delbert E. Gantz
Assistant Examiner—Joseph A. Boska

[57] ABSTRACT

Benzotrihalides are prepared by pyrolyzing a substituted phenyl trihaloacetate of the formula

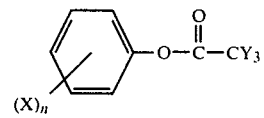

wherein each
X is halo, nitro, alkyloxy, aryloxy, aralkyoxy, cyano, lower alkyl, haloalkyl, haloalkyloxy, alkenyl, haloalkenyl, carbamoyl, N,N-dialkylcarbamoyl, N,N-diarylcarbamoyl, or N,N-diaralkyloxy;
Y is halo; and
n is an integer of from 1 to 5. As an example, 4-chlorophenyl trichloroacetate is pyrolyzed at 550° C. to 4-chlorobenzotrichloride.

16 Claims, No Drawings

PROCESS FOR PREPARING SUBSTITUTED BENZOTRIHALIDES

BACKGROUND OF THE INVENTION

The present invention relates generally to a process for producing organic halide compounds, and more in particular to a process for producing substituted benzotrihalide compounds.

Substituted benzotrihalide compounds are a known class of compounds used in various commercial applications. One of the most valuable applications is as an intermediate in making herbicides such as, for example, trifluralin, benefin, fluchlovalin, dinitramine, profluralin, ethyl fluralin, chloramber, 2,3,6-trichlorobenzoic acid, and the like.

Various methods have been employed to produce substituted benzotrihalides. In one method, 4-chlorobenzotrichloride was produced by a multi-step reaction starting with toluene. In this reaction, toluene was chlorinated in the presence of iron chloride at a temperature of from about 90° to about 100° C. to form an isomeric mixture of ortho- and para- chlorotoluene which was resolved by distillation. The para-isomer was then reacted with gaseous chlorine in the presence of ultraviolet light to chlorinate the side chain carbon of the chlorotoluene molecule. The resulting 4-chlorobenzotrichloride has been converted to 4-chlorobenzotrifluoride by methods such as that taught in U.S. Pat. No. 4,045,502.

In another method for producing 4-chlorobenzotrichloride, toluene was sulfonated with chlorosulfonic acid to form a mixture of the ortho- and para- isomers of toluenesulphonyl chloride. This isomeric mixture was resolved on the basis of melting points. The para-isomer was then converted to 4-chlorobenzotrichloride by allowing it to react with chlorine in an inert medium under irradiation with ultraviolet light as described in U.S. Pat. No. 3,230,268 and by B. Miller, and C. Walling in *J. Am. Chem. Soc.*, 79, 4187 (1957).

Nearly all the present industrial processes for producing the substituted benzotrihalides, especially the monosubstituted benzotrihalides, suffer from the disadvantage of producing a mixture of position isomers which must be resolved.

A need, therefore, exists for a process which produces good yields of the desired product while selectively controlling the production of position isomers, especially the ortho- and para-isomers of the monosubstituted compounds.

SUMMARY OF THE INVENTION

The present invention is a process for the production of substituted benzotrihalide compounds comprising pyrolyzing a substituted phenyl trihaloacetate of the formula:

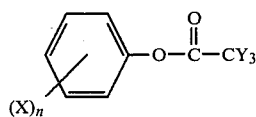

(I)

wherein each
X is halo, nitro, alkyloxy, aryloxy, aralkyloxy, cyano, lower alkyl, haloalkyl, haloalkyloxy, alkenyl, haloalkenyl, carbamoyl, N,N-dialkylcarbamoyl, N,N-diarylcarbamoyl, or N,N-diaralkyloxy;
Y is halo; and
n is an integer of from 1 to 5; to form a substituted benzotrihalide of the formula:

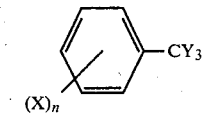

(II)

wherein X, Y, and n are as defined above.

The desired products are formed in high yields and purity.

DETAILED DESCRIPTION OF THE INVENTION

Substituted phenyl trihaloacetates of formula I are thermally converted to the corresponding substituted benzotrihalide compounds of formula II by pyrolysis. Pyrolysis is defined as the transformation of a compound into one or more other substances by heat alone. Preferably the pyrolysis takes place in the presence of an inert contact medium or catalyst. The reaction involves the cleavage of an aromatic carbon-oxygen bond with the elimination of carbon dioxide as illustrated by the equation:

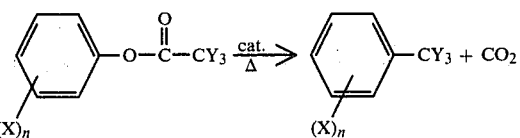

wherein X, Y, and n are defined above.

Illustrative examples of substituted phenyl trihaloacetates suitable as starting material in the process include the following:

4-bromophenyl trichloroacetate
4-n-butoxyphenyl trichloroacetate
2-chloro-4,5-dimethylphenyl trichloroacetate
2-chloro-5-methylphenyl trichloroacetate
2-chloro-4-nitrophenyl trichloroacetate
4-methylphenyl trichloroacetate
2-cyanophenyl trichloroacetate
2,4-dichlorophenyl trichloroacetate
2,6-diisopropylphenyl trichloroacetate
2,3-dimethoxyphenyl trichloroacetate
2,3-dimethylphenyl trichloroacetate
2,4-dinitrophenyl trichloroacetate
4-dimethylcarbamoyl phenyl trichloroacetate
4-carbamoylphenyl trichloroacetate
4-diphenyl carbamoylphenyl trichloroacetate
4-dibenzylcarbamoylphenyl trichloroacetate
3-methyl-4-nitrophenyl trichloroacetate
4-phenoxyphenyl trichloroacetate
4-benzyloxyphenyl trichloroacetate
4-nitrophenyl trichloroacetate
pentachlorophenyl trichloroacetate
4-trifluoroethenyl phenyl trichloroacetate
2,3,5-trichlorophenyl trichloroacetate
2,4,6-trimethylphenyl trichloroacetate
2,3,4,5-tetrachlorophenyl trichloroacetate
4-nitro-3-trifluoromethylphenyl trichloroacetate
3-trichloromethylphenyl trichloroacetate, and 4-vinylphenyl trichloroacetate. The corresponding tribromoacetate, trifluoroacetate, and mixed halo trihaloacetate compounds are also suitable as starting material. The 4-halosubstituted and the 2,4-dihalosubstituted trichloroacetates are preferred starting materials.

The substituted phenyl trihaloacetates are a known class of compounds. They are conveniently prepared by well-known techniques. For example, the mono-, di-, and tri- chlorophenyl esters of trichloroacetic acid can be prepared by the reaction described by B. Sledzenski, L. Creslakova and R. Malinowski, in *Przem. Chem.* 50, 171 (1971); Chemical Abstracts, 75:5379 (1971).

The pyrolysis of the substituted phenyl trihaloacetates is preferably carried out in the vapor phase. In this embodiment, liquid phenyl trihaloacetate in a stream of dry inert carrier gas (e.g. nitrogen) is heated to sufficient temperature to vaporize the substituted phenyl trihaloacetate. The vaporized material and carrier gas are then heated at a temperature sufficient to pyrolyze at least a portion of the vaporized substituted phenyl trihaloacetate. Generally, the higher the pyrolysis temperature the greater the likelihood of forming undesirable secondary products. Consequently, a pyrolysis temperature for the vapor phase reaction of from about 300° to about 750° C. is normally used. Preferably the pyrolysis temperature is from about 450° to about 650° C. More preferably the pyrolysis temperature is from about 450° C. to about 500° C.

The pyrolysis is preferably conducted under anhydrous conditions in the presence of an inert contacting medium such as glass rings, activated charcoal, graphite, mixtures thereof, and the like. More preferably the pyrolysis is conducted in the presence of a catalyst. The inorganic salts of strong Lewis acids and weak bases are suitable pyrolysis catalysts. Illustrative examples of such catalysts include, for example, $PdCl_2$, $SrNiPO_4$, $FeCl_3$, $CaSO_4$, $Ca_3(PO_4)_2$, $BaCl_2$, $CaCl_2$, $SrCl_2$, $KF$, $LaCl_3$, $ZrOCl_2$, $MgCl_2$, mixtures thereof, and the like. The use of a catalyst or contact medium is preferred because it advantageously lowers the required pyrolysis temperature, increases the yield of desired product, and allows for better selectivity in producing the desired product.

The pyrolysis is preferably carried out at substantially atmospheric pressure, however, greater or lesser pressures may be used, as desired.

The invention will be readily understood with reference to the following examples which are illustrative of the present invention.

EXAMPLE 1

Part A—Preparation of 4-chlorophenyl trichloroacetate

A 25.6 gram (g) (0.2 mole) sample of 4-chlorophenol was mixed with 40 g of trichloroacetyl chloride at room temperature. The resulting solution was heated under reflux conditions at 120° C. for 10 hours. The temperature was gradually increased to 180° C. over a period of 16 hours. The reaction mixture was then allowed to cool to room temperature. An insoluble solid product was collected by filtration and dried in vacuo. The solid was identified by vapor phase chromatography as 4-chlorophenyl trichloroacetate.

Part B—Preparation of 4-chlorobenzotrichloride

The 4-chlorophenyl trichloroacetate prepared in Part A was metered into a vaporization chamber at a rate of about 1 milliliter per minute ($6 \times 10^{-3}$ moles per minute) along with $12 \times 10^{-3}$ moles per minute of nitrogen and heated to about 300° C. The heated mixture was passed through a reactor at the indicated rate thereby providing a reactor residency time of about 1.2 seconds.

The reactor was a tubular structure constructed of Vycor ® brand glass and having an outside diameter of about 1 inch; an inside diameter of about ¾ inch and a length of about 36 inches. The interior of the reactor was packed with Vycor ® glass rings. The reactor temperature was controlled at 550° C. by a Pyrovane controller. The effluent gases from the reactor were passed through a water cooled condenser. The condensed reaction product was analyzed by vapor phase chromatography and was found to contain 48 percent by volume of the desired 4-chlorobenzotrichloride. The complete analysis of the reaction product and the operating conditions are described in Table 1.

EXAMPLES 2–20

In a manner substantially identical to that described in Example 1, various starting materials were pyrolyzed by the method of the present process. The starting material and reaction conditions are described in detail in Table 1.

The examples illustrate the variety of contact medium, catalysts, and reaction conditions that can be used in the present process to achieve a consistently high yield of the desired substituted benzotrihalides. A comparison of examples 4 and 12 illustrates the advantageous use of an inorganic salt as reaction catalysts.

TABLE 1

Pyrolysis of Substituted Phenyl Triahaloacetates

| Ex. | Starting Material | Catalyst | Temp. °C. | GLC Analysis of Reaction Products (In Area Percent) | | | | | Ratio of Primary to Secondary Products | % Conversion of Starting Material | % Yield* of Primary Product |
| --- | --- | --- | --- | --- | --- | --- | --- | --- | --- | --- | --- |
| | | | | Primary Product | Secondary Product | Ternary Product | Starting Material | Unknown | | | |
| 1 | 4-CCl$_3$—CO$_2\phi$Cl | Vycor Ring | 550 | 4-Cl$\phi$CCl$_3$ 17.0 | 4-Cl$_2\phi$ 11.6 | 4-CCl$_3$—O$\phi$Cl 2.0 | 64.8 | 4.6 | 1.5 | 35.2 | 48.3 |
| 2 | 4-CCl$_3$—CO$_2\phi$Cl | PdCl$_2$ (0.5%) on Act. Charcoal (mesh 10-20) | 500 | 4-Cl$\phi$CCl$_3$ 27.3 | 4-Cl$_2\phi$ 1.3 | — | 68.2 | 3.2 | 21.0 | 31.8 | 85.8 |
| 3 | 4-CCl$_3$—CO$_2\phi$Cl | PdCl$_2$ (0.5%) on Act. Charcoal (mesh | 550 | 4-Cl$\phi$CCl$_3$ 28.4 | 4-Cl$_2\phi$ 6.0 | — | 60.5 | 5.1 | 4.7 | 39.5 | 71.9 |

TABLE 1-continued

Pyrolysis of Substituted Phenyl Triahaloacetates

| Ex. | Starting Material | Catalyst | Temp. °C. | GLC Analysis of Reaction Products (In Area Percent) | | | | | Ratio of Primary to Secondary Products | % Conversion of Starting Material | % Yield* of Primary Product |
|---|---|---|---|---|---|---|---|---|---|---|---|
| | | | | Primary Product | Secondary Product | Ternary Product | Starting Material | Unknown | | | |
| 4 | 4-CCl$_3$—CO$_2\phi$Cl | Act. Charcoal (4–12 mesh) 10–20) | 550 | 4-Cl$\phi$CCl$_3$ 24.8 | 4-Cl$_2\phi$ 7.6 | — | 55.0 | 12.6 | 3.3 | 45.0 | 55.1 |
| 5 | 4-CCl$_3$—CO$_2\phi$Cl | ¼" Graphite Pellets | 500 | 4-Cl$\phi$CCl$_3$ 31.4 | 4-Cl$_2\phi$ 5.8 | 4-CCl$_3$—O$\phi$Cl 1.2 | 51.2 | 10.4 | 5.8 | 48.8 | 64.3 |
| 6 | 4-CCl$_3$—CO$_2\phi$Cl | ¼" Graphite Pellets | 510 | 4-Cl$\phi$CCl$_3$ 24.8 | 4-Cl$_2\phi$ 3.7 | 4-CCl$_3$O—$\phi$Cl 1.1 | 64.3 | 6.1 | 6.7 | 35.7 | 69.5 |
| 7 | 4-CCl$_3$—CO$_2\phi$Cl | ¼" SrNiPO$_4$ Pellets | 500 | 4-Cl$\phi$CCl$_3$ 27.9 | 4-Cl$_2\phi$ 1.0 | 4-CCl$_3$O—$\phi$Cl 1.4 | 58.6 | 12.7 | 28.0 | 43.4 | 64.2 |
| 8 | 4-CCl$_3$—CO$_2\phi$Cl | SrNiPO$_4$ | 500 | 4-Cl$\phi$CCl$_3$ 15.4 | 4-Cl$_2\phi$ 12.8 | 4-CCl$_3$O—$\phi$Cl 1.0 | 22.3 | 48.5 | 1.2 | 77.7 | 19.8 |
| 9 | 4-CCl$_3$—CO$_2\phi$Cl | 2% FeCl$_3$ on Graphite | 450 | 4-Cl$\phi$CCl$_3$ 26.6 | 4-Cl$_2\phi$ 1.1 | 4-CCl$_3$O—$\phi$Cl 0.4 | 51.3 | 18.6 | 24.0 | 48.7 | 54.6 |
| 10 | 4-CCl$_3$—CO$_2\phi$Cl | CaSO$_4$ (8 mesh) | 500 | 4-Cl$\phi$CCl$_3$ 0.9 | 4-Cl$_2\phi$ 15.3 | 4-Cl$\phi$C(=O)—Cl 65.0 | 3.4 | 15.3 | .1 | 96.6 | 1.0 |
| 11 | 4-CCl$_3$—CO$_2\phi$Cl | Ca$_3$(PO$_4$)$_2$ (4–12 mesh) | 480 | 4-Cl$\phi$CCl$_3$ 31.8 | 4-Cl$_2\phi$ 12.6 | 4-Cl$\phi$C(=O)—Cl 2.8 | 47.3 | 5.6 | 2.5 | 52.7 | 60.3 |
| 12 | 4-CCl$_3$—CO$_2\phi$Cl | BaCl$_2$ on 4–10 mesh Act. Char. | 470 | 4-Cl$\phi$CCl$_3$ 47.2 | 4-Cl$_2\phi$ 6.1 | 4-CCl$_3$O—$\phi$Cl 0.8 | 37.5 | 8.4 | 7.7 | 62.5 | 75.4 |
| 13 | 4-CCl$_3$—CO$_2\phi$Cl | CaCl$_2$ (4 mesh) | 490 | 4-Cl$\phi$CCl$_3$ 62.0 | 4-Cl$_2\phi$ 9.5 | — | 24.0 | 4.5 | 6.5 | 76.0 | 81.6 |
| 14 | 4-CCl$_3$—CO$_2\phi$Cl | CaCl$_2$ (4 mesh) | 490 | 4-Cl$\phi$CCl$_3$ 55.0 | 4-Cl$_2\phi$ 8.5 | — | 31.0 | 5.5 | 6.0 | 69.0 | 79.7 |
| 15 | 4-CCl$_3$—CO$_2\phi$Cl | CaCl$_2$ (4 mesh) | 490 | 4-Cl$\phi$CCl$_3$ 52.0 | 4-Cl$_2\phi$ 8.0 | — | 35.0 | 5.0 | 5.7 | 65.0 | 80.0 |
| 16 | CCl$_3$CO$_2$—$\phi$Cl$_2$ | Activated Charcoal (mesh 4–12) | 550 | 2,4-diCl-benzo trichloride 9.9 | 1,2,4-tri-Cl$\phi$ 4.3 | Cl$_2\phi$OH 2.0 | 80.2 | 3.6 | 2.3 | 19.8 | 50.0 |
| 17 | CCl$_3$CO$_2$—$\phi$Cl$_2$ | ¼" Graphite Pellets | 500 | 2,4-diCl-benzo trichloride 24.7 | 1,2,4-tri-Cl$\phi$ 10.8 | CCl$_3$O—$\phi$Cl$_3$ 0.6 Cl$_2\phi$OH 2.4 | 56.0 | 5.5 | 2.3 | 44.0 | 56.2 |
| 18 | CCl$_3$CO$_2$—$\phi$Cl$_2$ | ¼" Graphite Pellets | 500 | 2,4-diCl-benzo trichloride 23.0 | 1,2,4-tri-Cl$\phi$ 4.2 | CCl$_3$O—$\phi$Cl$_2$ 0.6 Cl$_2\phi$OH 3.0 | 66.2 | 3.0 | 5.5 | 33.0 | 68.0 |
| 19 | 4-CF$_3$CO$_2\phi$Cl | — | 650 | 4-Cl$\phi$CF$_3$ 8.0 | 4-Cl$_2\phi$ 0.9 | — | 87.8 | 3.3 | 8.8 | 12.2 | 65.6 |
| 20 | CCl$_2$CO$_2$—$\phi$Cl$_2$ | CaCl$_2$ (4 mesh) | 465 | 2,4-diCl benzotrichloride 40.0 | 1,2,4-Cl$_3\phi$ 15.0 | CCl$_3$COCl 17.0 | 28.0 | — | 2.6 | 80.0 | 50.0 |

Notes:
*% yield based on material converted
4-CCl$_3$CO$_2\phi$Cl = 4-chlorophenyl trichloroacetate
4-Cl$_2\phi$ = 1,4-dichlorobenzene
4-CCl$_3\phi$Cl = 4-chlorobenzotrichloride
4-CCL$_3$O$\phi$Cl = 4-trichloromethoxy chlorobenzene $$\text{4-Cl}\phi\overset{\text{O}}{\underset{\|}{\text{C}}}\text{—Cl} = \text{4-chlorobenzoyl chloride}$$

CCl$_3$CO$_2\phi$Cl = 4-chlorophenyl trichloroacetate
1,2,4-triCl$\phi$ = 1,2,4-trichlorobenzene
Cl$_2\phi$OH = 2,4-dichlorophenol
CCl$_3$O$\phi$Cl$_2$ = 2,4-dichlorophenyl trichloromethyl ether
4-CF$_3$CO$_2\phi$Cl = 4-chlorophenyl trifluoroacetate
4-Cl$\phi$CF$_3$ = 4-chlorobenzo trifluoride

What is claimed is:
1. A process for producing a substituted benzotrihalide compound comprising pyrolyzing a substituted phenyl trihaloacetate of the formula

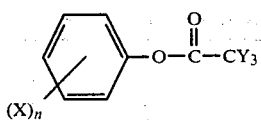

wherein each
X is halo, nitro, alkyloxy, aryloxy, aralkyloxy, cyano, lower alkyl, haloalkyl, haloalkyloxy, alkenyl, haloalkenyl, carbamoyl, N,N-dialkylcarbamoyl, N,N-diarylcarbamoyl, or N,N-diaralkyloxy;
Y is halo; and
n is an integer of from 1 to 5; to form a substituted benzotrihalide of the formula

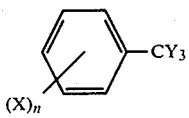

wherein X, Y, and n are defined above.

2. The process of claim 1 wherein the pyrolysis temperature is from about 300° to about 750° C.

3. The process of claim 1 wherein the pyrolysis temperature is from about 450° to about 650° C.

4. The process of claim 1 wherein the pyrolysis temperature is from about 450° to about 500° C.

5. The process of claim 1 wherein the pyrolysis is conducted in the presence of an inert contact medium or catalyst.

6. The process of claim 5 wherein the inert contact medium is selected from the group consisting of glass rings, activated charcoal, graphite, and mixtures thereof.

7. The process of claim 5 wherein the pyrolysis is conducted in the presence of a catalyst.

8. The process of claim 7 wherein the catalyst is an inorganic salt.

9. The process of claim 8 wherein the inorganic salt is selected from the group consisting of $PdCl_2$, $SrNiPO_4$, $FeCl_3$, $CaSO_4$, $Ca_3(PO_4)_2$, $BaCl_2$, $CaCl_2$, $SrCl_2$, $KF$, $LaCl_3$, $ZrOCl_2$, $MgCl_2$, and mixtures thereof.

10. The process of claim 1 wherein I is 4-chlorophenyl trichloroacetate.

11. The process of claim 1 wherein I is 2,4-dichlorophenyl trichloroacetate.

12. The process of claim 1 wherein I is 4-chlorophenyl trifluoroacetate.

13. The process of claim 1 wherein the pyrolysis is conducted under anhydrous conditions.

14. A process for producing a substituted benzotrihalide compound comprising:
(a) vaporizing a substituted phenyl trihaloacetate of the formula:

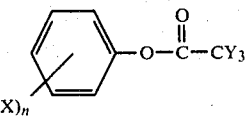

wherein each
X is halo, nitro, alkyloxy, aryloxy, aralkyloxy, cyano, lower alkyl, haloalkyl, haloalkyloxy, alkenyl, haloalkenyl, carbamoyl, N,N-dialkylcarbamoyl, N,N-diarylcarbamoyl, or N,N-diaralkyloxy;
Y is halo; and
n is an integer of from 1 to 5,
(b) heating said vaporized substituted phenyl trihaloacetate in the presence of a catalyst to a sufficient temperature to thermally convert at least a portion of said substituted phenyl trihaloacetate to the corresponding substituted benzotrihalide compound of the formula

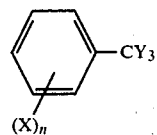

wherein
X, Y, and n are defined above, and
(c) recovering said substituted benzotrihalide compound.

15. The process of claim 14 wherein the vaporized substituted phenyl trihaloacetate is contained in an inert carrier gas.

16. A process for producing a substituted benzotrihalide compound comprising:
(a) vaporizing 4-chlorophenyl trichloroacetate;
(b) heating said vaporized 4-chlorophenyl trichloroacetate in the presence of particulate calcium chloride to a temperature of about 490° C. to thermally convert at least a portion of the 4-chlorophenyl trichloroacetate to 4-chlorobenzotrichloride.

* * * * *